(12) United States Patent
Lee et al.

(10) Patent No.: US 7,297,950 B2
(45) Date of Patent: Nov. 20, 2007

(54) TRANSMISSION ELECTRON MICROSCOPE SPECIMEN AND METHOD OF MANUFACTURING THE SAME

(75) Inventors: Myoung-Rack Lee, Suwon-si (KR); Jung-Sun Kim, Suwon-si (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 0 days.

(21) Appl. No.: 11/241,953

(22) Filed: Oct. 4, 2005

(65) Prior Publication Data
US 2006/0097168 A1   May 11, 2006

(30) Foreign Application Priority Data
Oct. 26, 2004  (KR) .................... 10-2004-0085576

(51) Int. Cl.
*G01N 23/00*  (2006.01)
*G21K 7/00*   (2006.01)
(52) U.S. Cl. ........................ 250/311; 438/33
(58) Field of Classification Search ........... 438/460, 438/33; 250/311, 442; 977/881
See application file for complete search history.

(56) References Cited

U.S. PATENT DOCUMENTS

| 5,892,225 A * | 4/1999 | Okihara ............ 250/311 |
| 6,184,064 B1 * | 2/2001 | Jiang et al. ........ 438/113 |
| 6,538,254 B1 * | 3/2003 | Tomimatsu et al. ... 250/442.11 |

FOREIGN PATENT DOCUMENTS

| JP | 2004-042215 | 2/2004 |
| KR | 100209658 | 4/1999 |
| KR | 100214551 | 5/1999 |
| KR | 100253320 | 1/2000 |
| KR | 1020030043233 | 6/2003 |

* cited by examiner

*Primary Examiner*—Georgia Epps
*Assistant Examiner*—Francis M. LeGasse, Jr.
(74) *Attorney, Agent, or Firm*—Volentine & Whitt, PLLC (57) ABSTRACT

A transmission electron microscope (TEM) specimen and a method of manufacturing the specimen are provided. The specimen comprises an analysis point. The specimen is formed by forming a dimple at a surface portion of the preliminary specimen, and ion milling the preliminary specimen having the dimple.

19 Claims, 9 Drawing Sheets

TRANSMISSION ELECTRON MICROSCOPE SPECIMEN AND METHOD OF MANUFACTURING THE SAME

BACKGROUND OF THE INVENTION

1. Field of the Invention

Embodiments of the invention relate to a transmission electron microscope (TEM) specimen and a method of manufacturing the specimen. More particularly, embodiments of the invention relate to a method of forming a dimple on a TEM specimen and a method of manufacturing the specimen.

This application claims priority to Korean Patent Application No. 2004-85576, filed on Oct. 26, 2004, the subject matter of which is hereby incorporated by reference in its entirety.

2. Description of the Related Art

In general, manufacturing a semiconductor device comprises several processes, such as a diffusion process, an oxidation process, a sputtering process, etc. These processes are performed repeatedly on a semiconductor substrate to stack layers on the substrate. A layer may be, for example, a metal layer such as an aluminum layer, a titanium layer, tungsten layer, etc., or an insulation layer such as a nitride layer, an oxide layer, etc. As semiconductor devices have become more highly integrated and their components have become increasingly smaller, the process of manufacturing a semiconductor device has become more complex.

When any one of the layers formed on a semiconductor substrate is defective (e.g., abnormally formed), the semiconductor device will typically fail to operate properly. In such circumstances, it is necessary to accurately and effectively analyze the defective layer, or at least determine whether the layer is defective or not. A TEM is often used to analyze a potentially defective layer. Conventional TEMs focus an electron beam on a specimen under examination to analyze a potentially effective layer in the specimen. An image of the layer under examination is obtained from the irradiating electron beam. More particularly, an electron diffraction pattern is obtained as the irradiating electron beam is diffracted by the constituent components of the layer being examined. In this manner, the conventional TEM analyzes the crystalline structure of the layer based on the resulting electron diffraction pattern.

To analyze a layer using a TEM, a suitable specimen must be properly prepared. There are many conventional methods and constituent processing steps involved in the preparation of a TEM specimen. Argon ion milling, chemical polishing, chemical etching, using a cleavage system, and electro polishing—all or individually applied to a specimen in accordance with the material properties of its stacked layers and the nature of the analysis point under examination—are typical method steps adapted to the preparation of a TEM specimen. Argon ion milling has been widely employed in the preparation of TEM specimens adapted to the examination of stacked layers formed on a semiconductor substrate and the interfaces between the stacked layers.

As noted above, a TEM obtains information about a specimen from an image generated by the transmission of an accelerated electron beam through the specimen. Thus, the specimen must be relatively thin, at least in the portion being specifically examined by the electron beam. In addition, the specimen must be prepared without scratches or contaminants. Thus, various methods have been studied to effectively prepare TEM specimens.

For example, one method of manufacturing a specimen for TEM examination is disclosed in Korean Patent No. 209658. According to the method disclosed in Korean Patent No. 209658, a rotational angle of the specimen is adjusted in accordance with a difference between average atomic weights for each of stacked layers or the difference between sputtering speeds used to fabricate each of the stacked layers. This ion milling process produces a specimen having a more uniform thickness, and may be completed in a relatively short time.

Another method of manufacturing a planar wafer specimen for testing is also disclosed in Korean Patent No. 253320. According to the method disclosed in Korean Patent No. 253320, marks on the planar specimen are used (e.g., visualized) in order to analyze the cross sectional state and surface state of a specific region in the wafer specimen (e.g., a specific layer formed on the wafer as captured within the specimen).

One conventional method of manufacturing a specimen comprises; a cutting process, a bonding process, a slicing process, a punching process, a grinding process, a dimpling process and an ion-milling process. In the cutting process, first and second preliminary specimens and first, second, third, and fourth dummy wafers are prepared. In the bonding process, a first face of the first preliminary specimen is formed on a first face of the second preliminary specimen. The first and second dummy wafers and the third and fourth dummy wafers are formed on second faces of the first and second preliminary specimens, respectively, to form a stacked specimen. The second faces of the first and second preliminary specimens are opposite the first faces of the first and second preliminary specimens, respectively. In the slicing process, the stacked specimen is cut using a diamond saw to form a rectangular specimen having a thickness of about 0.5 mm to about 1 mm. In the punching process, the rectangular specimen is punched to form a circular specimen having a diameter of about 3 mm. In the grinding process, both circular faces of the circular specimen are ground using a grinder or a polisher to form a final specimen having a thickness of no more than about 100 µm. In the dimpling process, a dimple is formed at a central portion of the final specimen so that the thickness of the central portion of the final specimen is no more than about 1 µm. In the ion-milling process, both sides of the final specimen are sputtered with argon ions to form a hole through the central portion of the final specimen, thereby completing the formation of the final specimen. The final specimen is held by a holder adapted for use with a TEM and is placed on a corresponding support. The hole of the final specimen is then visualized and analyzed.

Figure 1:
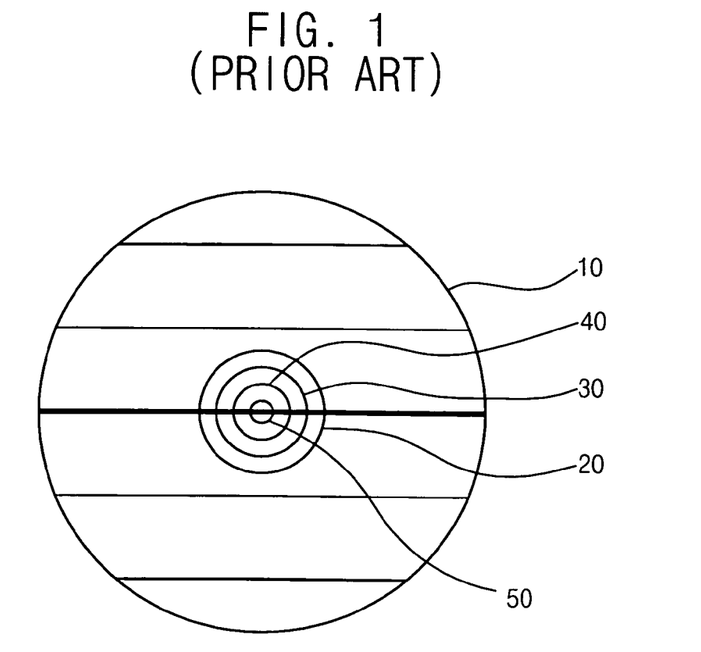
FIG. 1 is a cross sectional view illustrating a conventional TEM specimen.

Figure (FIG.) 1 is a cross sectional view illustrating a conventional TEM specimen.

Referring to FIG. 1, a first grinding region 20, a second grinding region 30, a third grinding region 40 and an ion-milling region 50 are formed concentrically around a central portion of a cross section of a specimen 10. Here, first grinding region 20 has a first diameter longer than a second diameter of second grinding region 30. The second diameter of second grinding region 30 is longer than a third diameter of third grinding region 40. Ion-milling region 50 has a fourth diameter shorter than the third diameter of third grinding region 40, and ion-milling region 50 is a hole used in observing specimen 10.

Figure 2:
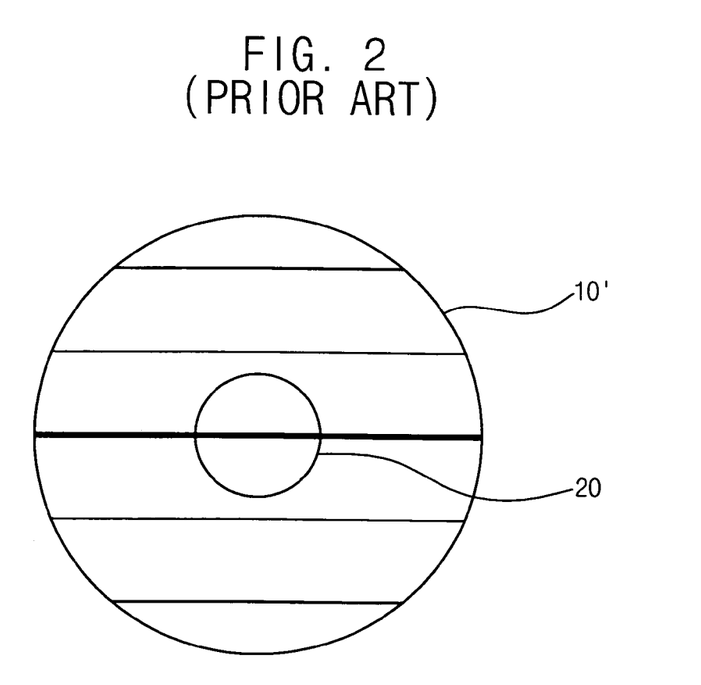
FIGS. 2 to 4 are cross sectional views illustrating a conventional method of forming a dimple on a TEM specimen.
Figure 3:
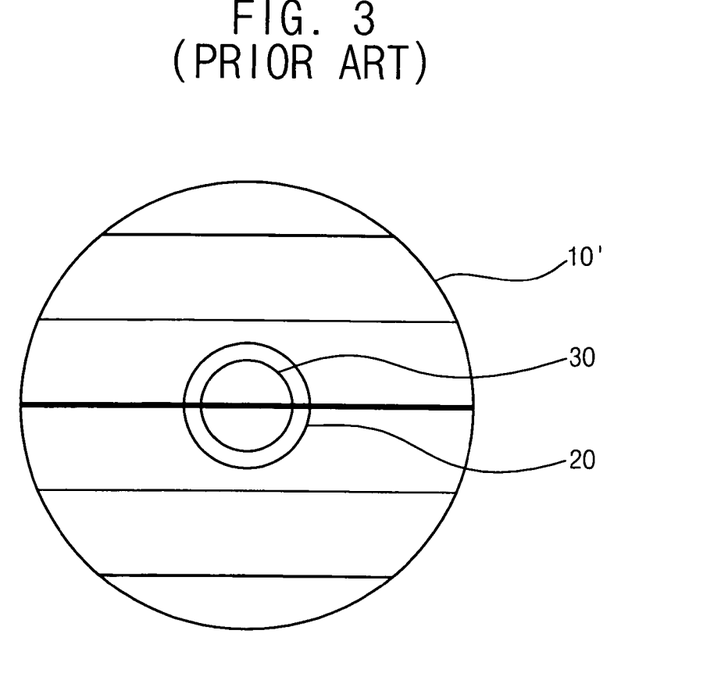
Figure 4:
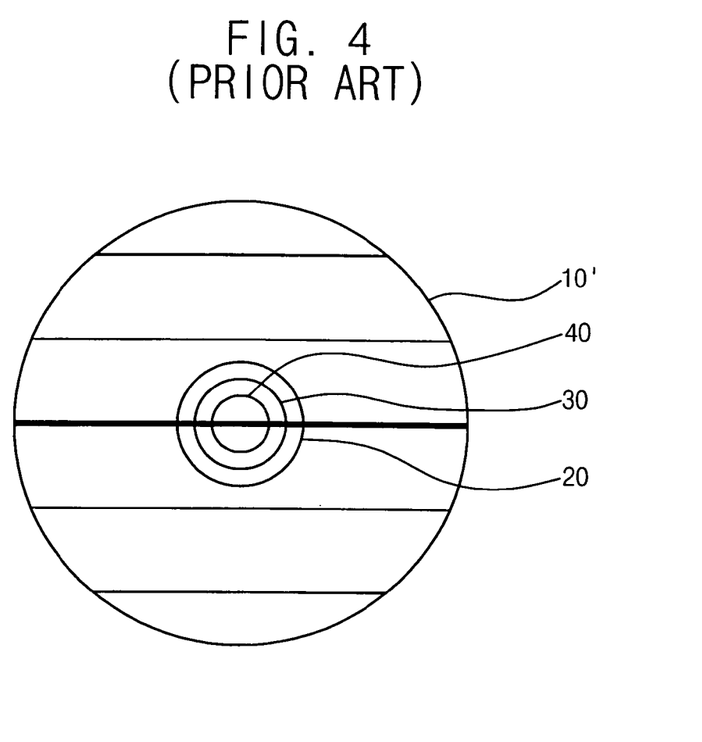

A conventional method of forming a dimple on a preliminary specimen is described in relation to FIGS. 2 to 4.

Referring to FIG. 2, a central portion of a cross section of a preliminary specimen 10', formed by stacking wafers, is ground using a bronze wheel to form first circular grinding region 20 having the first diameter. Here, the formation of the first grinding region 20 is carried out until red light is observed in a transmission scope.

Referring to FIG. 3, the central portion of preliminary specimen 10' is ground using a coarse wheel to form second grinding region 30 having the second diameter. Second grinding region 30 is concentric with first grinding region 20. Here, the formation of second grinding region 30 is carried out until orange light is observed in the transmission scope.

Referring to FIG. 4, the central portion of preliminary specimen 10' is repeatedly ground using a fine wheel to form third grinding region 40 having the third diameter. Third grinding region 40 is concentric with first and second grinding regions 20 and 30. Here, the formation of third grinding region 40 is carried out until yellow light or white light is observed in the transmission scope.

Figure 5:
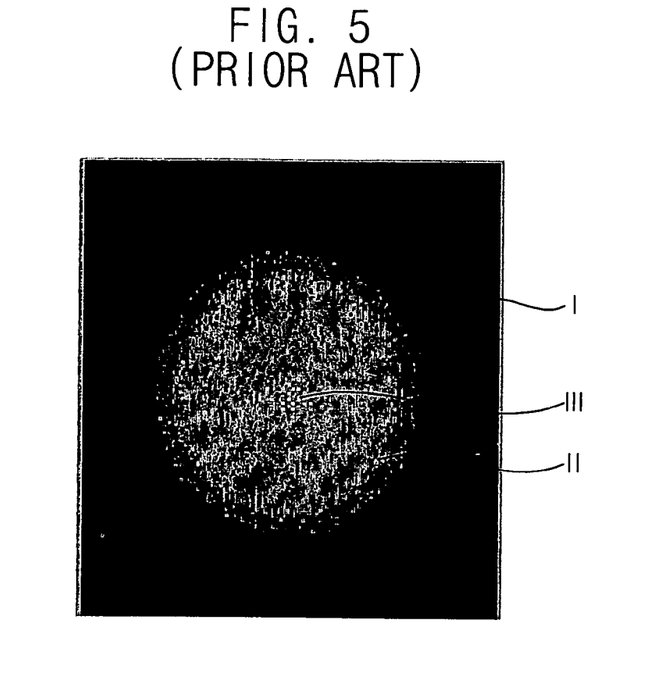
FIG. 5 is a picture illustrating a ground state of a specimen during formation of a dimple using a conventional method.

FIG. 5 is a transmission scope picture illustrating a conventional specimen having a dimple.

Referring to FIG. 5, the red light serving as reference light in forming first grinding region 20 is exhibited in a first region I corresponding to an edge region of specimen 10. The yellow light serving as reference light in forming third grinding region 40 is exhibited in a third region III corresponding to a central region of specimen 10. The orange light serving as reference light in forming second grinding region 30 is exhibited in a second region II between first region I and third region III.

To analyze the cross section of specimen 10 using a TEM, a central portion of third grinding region 40, which is the thinnest portion of preliminary specimen 10', is aligned with a central portion of preliminary specimen 10' in forming the dimple. Here, an analysis region of specimen 10 has an allowable diameter of about 30 μm to about 50 μm.

However, when the central portion of third grinding region 40 is not aligned with the central portion of preliminary specimen 10', the diameter of the analysis region of specimen 10 is smaller than the allowable diameter. Also, when hole 50 has a relatively large diameter, the analysis region in third grinding region 40 has a relatively small area.

SUMMARY OF THE INVENTION

In one embodiment, the invention provides a TEM specimen comprising an analysis region comprising an analysis point, and a peripheral region enclosing the analysis region. The analysis region comprises a dimple region, and an ion-milling region, located at a central portion of the dimple region, comprising two separate holes having the analysis point between them.

In another embodiment, the invention provides a method of manufacturing a TEM specimen comprising preparing a preliminary specimen, and forming a specimen by forming a dimple region on a surface portion of the preliminary specimen, and ion milling the preliminary specimen having the dimple region to form an ion-milling region comprising two separate holes having an analysis point between them.

BRIEF DESCRIPTION OF THE DRAWINGS

Exemplary embodiments will be described with reference to the accompanying drawings, in which like reference symbols indicate like components. In the drawings:

FIG. 11 is a picture illustrating a ground state of a specimen during formation of a dimple using a method that is in accordance with an exemplary embodiment of the invention; and, FIGS. 12 to 17 illustrate a method of manufacturing the specimen of FIG. 6 in accordance with an exemplary embodiment of the invention, wherein FIG. 12 is a plain view and FIGS. 13 to 17 are cross sectional views.

DESCRIPTION OF EXEMPLARY EMBODIMENTS

It will be understood that when an element or layer is referred to as being "on" another element or layer, it can be directly on the other element or layer, or intervening elements or layers may be present.

Figure 6:
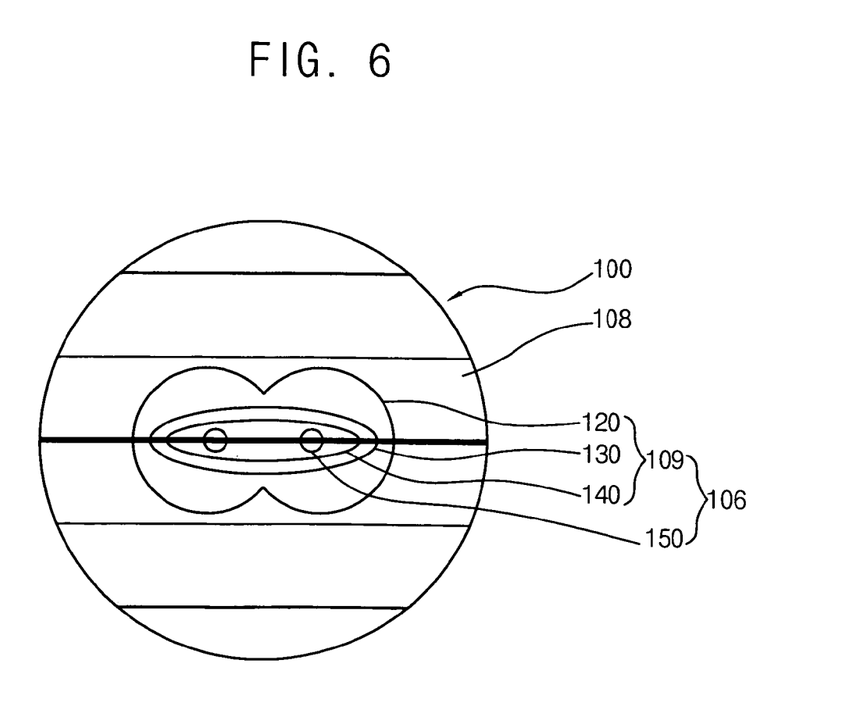
FIG. 6 is a cross sectional view illustrating a TEM specimen in accordance with an exemplary embodiment of the invention.

FIG. 6 is a cross sectional view illustrating a TEM specimen in accordance with an exemplary embodiment of the invention.

Referring to FIG. 6, a specimen 100 is in the shape of a disk, wherein the disk has a diameter of about 3 mm and a thickness of about 70 μm. An analysis region 106, formed on specimen 100, is centered at the center point of specimen 100.

A peripheral region 108 corresponds to the entire region of specimen 100 surrounding analysis region 106. Peripheral region 108 is formed along an outer boundary of analysis region 106 and encloses analysis region 106.

Analysis region 106 comprises a dimple region 109, and an ion-milling region 150 positioned at a central portion of dimple region 109.

Dimple region 109 further comprises a first grinding region 120, a second grinding region 130 and a third grinding region 140.

An analyzing direction is a direction from the analysis point toward the edge of a specimen or a preliminary specimen that is substantially parallel to the faces of the wafers used in the formation of the specimen or preliminary specimen. There are necessarily two analyzing directions, wherein a first analyzing direction is opposite a second analyzing direction. A line of analysis is a line that extends away from the analysis point of a specimen or a preliminary specimen in both of the analyzing directions.

First grinding region 120 has a first area, a first length substantially along the line of analysis, and a first width smaller than the first length that is substantially perpendicular to the line of analysis. In this exemplary embodiment, first grinding region 120, as shown in FIG. 6, has an overlapping circular shape.

As used herein, an overlapping circular shape is the shape of two partially overlapping circular shapes, as shown, for example, by first grinding region 120 of FIG. 6. The two overlapping circular shapes may overlap in the analyzing directions and/or with respect to the analysis point.

Alternatively, first grinding region 120 may have an elliptical shape, having its major axis substantially along the line of analysis. First grinding region 120 may also have another shape, having a first length substantially along the line of analysis and a first width substantially perpendicular to the line of analysis.

Second grinding region 130 has a second area smaller than the first area of first grinding region 120, a second length substantially along the line of analysis, and a second width smaller than the second length that is substantially perpendicular to the line of analysis. In this exemplary embodiment, second grinding region 130 has an elliptical shape. Alternatively, second grinding region 130 may have an overlapping circular shape.

Third grinding region 140 has a third area smaller than the second area of second grinding region 130, a third length substantially along the line of analysis, and a third width smaller than the third length that is substantially perpendicular to the line of analysis. Here, the third length of third grinding region 140 may be about 50 µm to about 150 µm. In this exemplary embodiment, third grinding region 140 has an elliptical shape. Alternatively, third grinding region 140 may have an overlapping circular shape.

Ion-milling region 150 comprises two separate holes that are within third grinding region 140 and have an analysis point between them. Specimen 100 is analyzed using the two holes.

In accordance with this exemplary embodiment, specimen 100 has a relatively large analysis area.

Hereinafter, a method of manufacturing specimen 100 will be described in detail.

Figure 7:
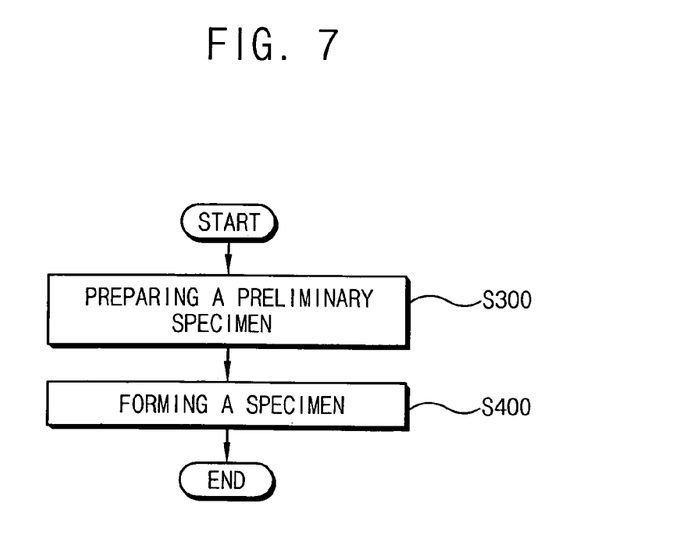
FIGS. 7 to 10 are flow charts illustrating a method of manufacturing the specimen of FIG. 6.
Figure 8:
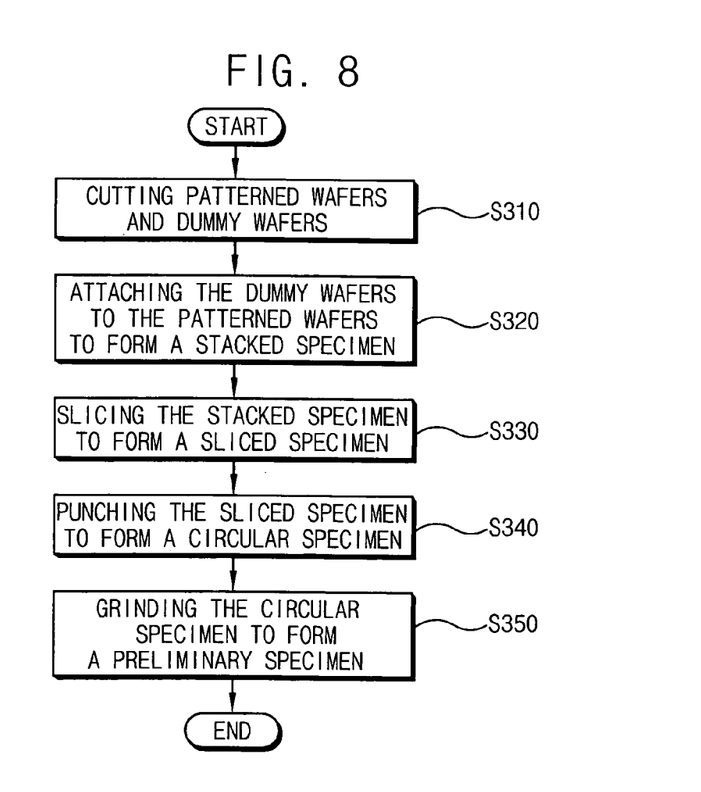
Figure 9:
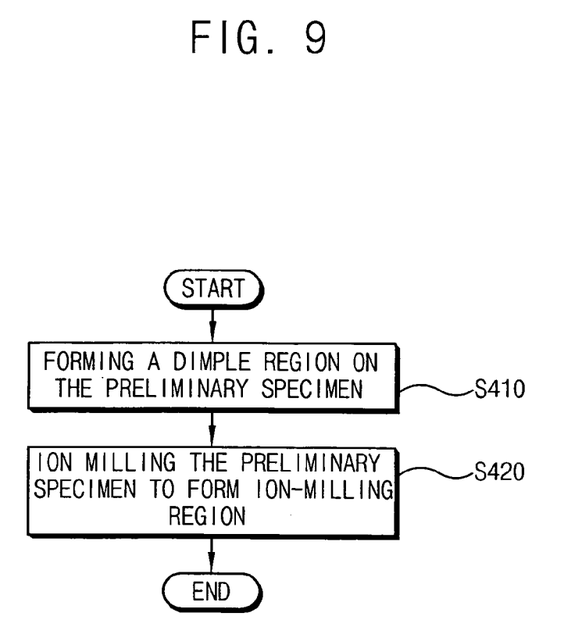
Figure 10:
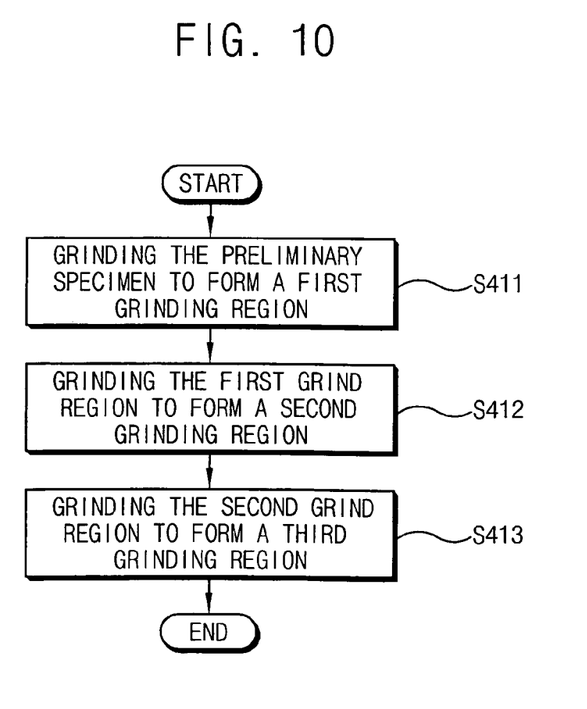

FIGS. 7 to 10 are flow charts illustrating a method of manufacturing specimen 100 of FIG. 6. FIG. 7 is a flow chart illustrating a method of manufacturing the specimen, FIG. 8 is a flow chart illustrating a method of forming a preliminary specimen, FIG. 9 is flow chart illustrating a method of forming a specimen from a preliminary specimen, and FIG. 10 is a flow chart illustrating a method of forming a dimple on a preliminary specimen.

Figure 11:
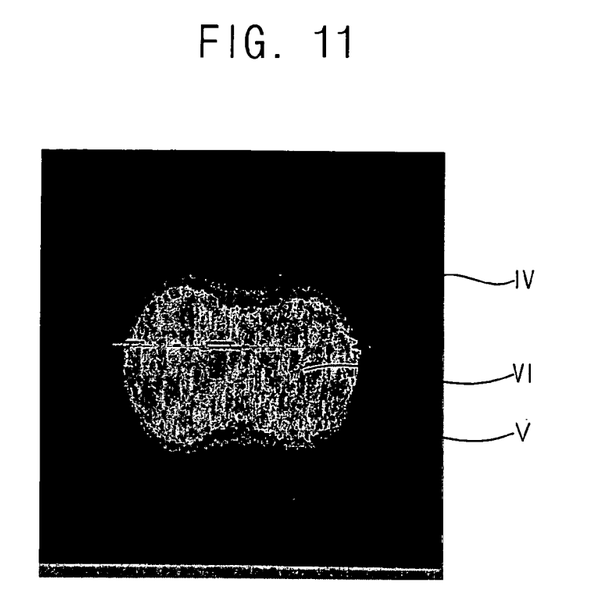

FIG. 11 is a picture illustrating a ground state of a specimen during formation of a dimple using a method that is in accordance with an exemplary embodiment of the invention.

Figure 12:
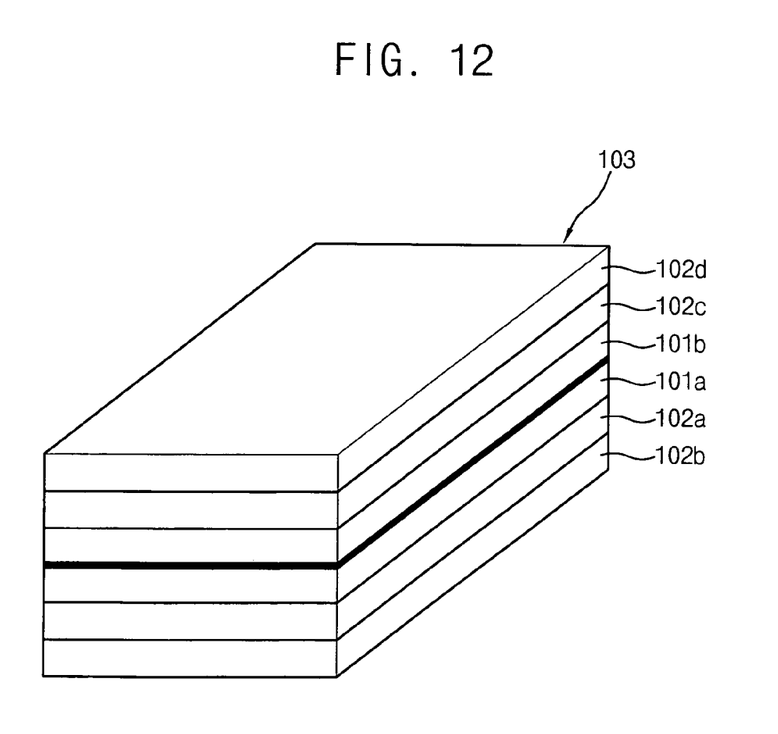
Figure 13:
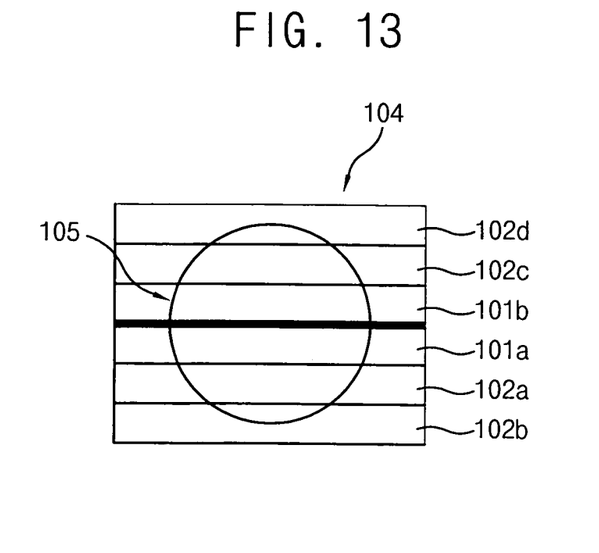

FIGS. 12 to 17 illustrate a method of manufacturing specimen 100 of FIG. 6. FIGS. 12 and 13 illustrate a method of forming the preliminary specimen, where FIG. 12 is a plain view and FIG. 13 is a cross sectional view. FIGS. 14 to 17 are cross sectional views illustrating a method of forming the specimen.

Referring to FIG. 7, a method of manufacturing specimen 100 for the TEM comprises preparing a preliminary specimen 110 (300) and forming a specimen 100 (400) by grinding preliminary specimen 110.

Hereinafter, preparing preliminary specimen 110 (300) will be described in detail.

Referring to FIGS. 8 and 12, first and second separated specimens 101a and 101b, and first, second, third, and fourth dummy wafers 102a, 102b, 102c and 102d are formed through a cutting process (310).

In particular, a patterned wafer, such as a semiconductor substrate on which a pattern to be analyzed is formed, is prepared. A cross section of the pattern on the semiconductor substrate is observed using an electron microscope to determine the analysis point of the pattern. The semiconductor substrate is then cut using a dicing saw to form first and second separated specimens 101a and 101b each having an area of about 4 mm×about 5 mm. In addition, wafers are cut to form first, second, third, and fourth dummy wafers 102a, 102b, 102c and 102d, each of which has an area substantially the same as that of first and second separated specimen 101a or 101b.

Then, to form a stacked specimen 103, first and second dummy wafers 102a and 102b are formed on first separated specimen 101a, and third and fourth dummy wafers 102c and 102d are formed on second separated specimen 101b (320).

In detail, a first face of first separated specimen 101a is formed on a first face of second separated specimen 10b. First and second dummy wafers 102a and 102b are each formed on a second face of first separated specimen 101a, which is opposite the first face of first separated specimen 101a, using a G1-epoxy resin. Third and fourth dummy wafers 102c and 102d are each formed on a second face of second separated specimen 101b, which is opposite the first face of second separated specimen 101b, using a G1-epoxy resin, thereby forming stacked specimen 103. Stacked specimen 103 is then compressed using a compressor to spread the G-epoxy resin widely and thinly. Next, stacked specimen 103 is heated to a temperature of about 145° C., thereby completing the construction of stacked specimen 103.

Referring to FIGS. 8 and 13, stacked specimen 103 is sliced in a direction substantially perpendicular to the faces of the wafers using a diamond cutter to form a sliced specimen 104 (330) having a thickness of about 0.5 mm to about 1 mm.

Sliced specimen 104 is then punched to form a circular specimen 105 (340) having a diameter of about 3 mm.

Next, both circular faces of circular specimen 105 are ground, using a grinder or a polisher, to form preliminary specimen 110 (350) having a thickness of about 70 µm.

Hereinafter, a method of forming specimen 100 from preliminary specimen 110 is described in detail.

Referring to FIG. 7, forming specimen 100 (400) comprises, referring to FIG. 9, forming a dimple on preliminary specimen 110 (410), and then ion milling preliminary specimen 110 (420).

Figure 14:
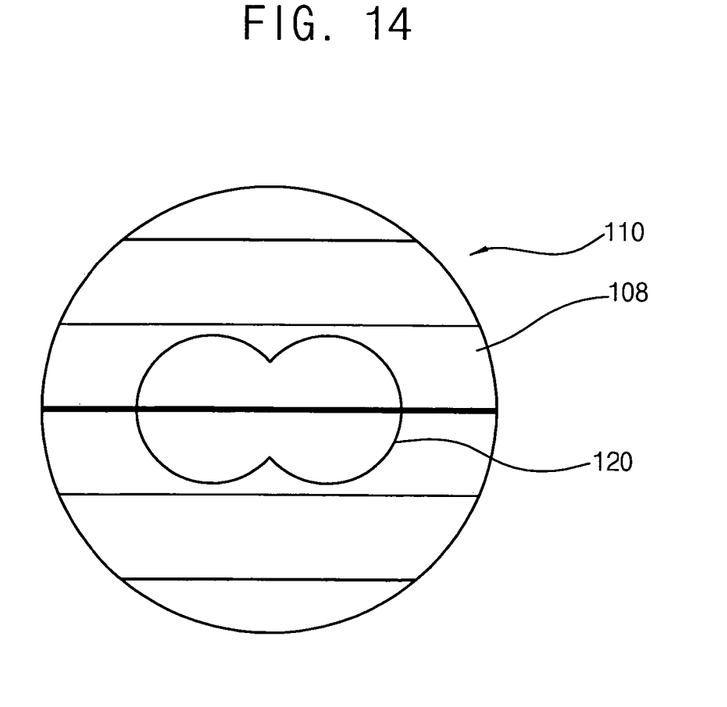

Forming a dimple on preliminary specimen 110 (410) comprises, referring to FIGS. 10 and 14, forming the first grinding region (411).

In particular, preliminary specimen 110 is ground in the analyzing directions from the analysis point to form first grinding region 120. First grinding region 120 has the first area, the first length substantially along the line of analysis, and the first width smaller than the first length that is substantially perpendicular to the line of analysis. In this exemplary embodiment, first grinding region 120 has an overlapping circular shape, as shown in FIG. 14.

Alternatively, first grinding region 120 may have an elliptical shape having its major axis substantially along the line of analysis. Peripheral region 108 corresponds to the entire region of preliminary specimen 110 surrounding first grinding region 120.

The thickness of preliminary specimen 110 at the dimple is not more than about 1 µm. This reduced thickness at the dimple is formed by polishing a cross section of the specimen using a chemical mechanical polishing (CMP) process. The process for forming the dimple is carried out using various abrasives in a series of steps. The abrasive used to form each grinding region may vary in accordance with the desired thickness of that grinding region.

Preliminary specimen 110 is ground using a dual grinding wheel to form first grinding region 120 (411) having a thickness of about 10 µm to about 20 µm. The thickness of a grinding region, as used herein, means the thickness of the specimen or preliminary specimen at that grinding region, excluding the portion of that grinding region that contains other grinding regions or an ion-milling region.

Here, when first grinding region 120 has a thickness of below about 10 µm, red light is observed in first grinding region 120 using a transmission scope. Thus, to form first grinding region 120, preliminary specimen 110 is ground until red light is observed.

Referring to FIG. 11, the red light exhibited in an edge region IV of preliminary specimen 110 serves as a reference in forming first grinding region 120. The yellow light exhibited in a central region VI of preliminary specimen 110 serves as a reference in forming third grinding region 140. The orange light exhibited in an interface region V between edge region IV and central region VI serves as a reference in forming second grinding region 130.

Since the process for forming first grinding region 120 is a fundamental process in forming the dimple, the process for forming first grinding region 120 need not be precise, and thus diamond particles may be used in forming first grinding region 120.

The method of forming the dimple further comprises grinding first grinding region 120 to form second grinding region 130 (412).

Figure 15:
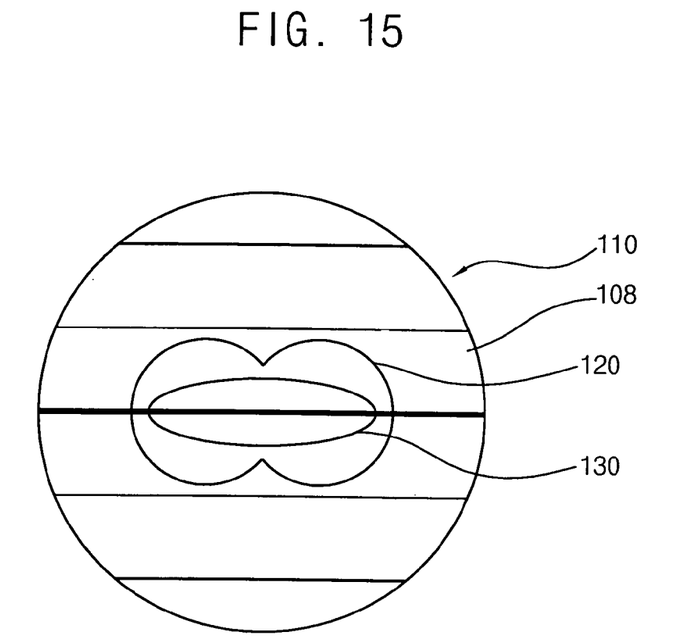

Referring to FIGS. 10 and 15, first grinding region 120 is ground with respect to the analysis point to form second grinding region 130 having an elliptical shape that has the second area smaller than the first area of first grinding region 120. The major axis of second grinding region 130 is substantially along the line of analysis of preliminary specimen 110.

In this exemplary embodiment, first grinding region 120 is ground using an abrasive comprising about 80% by weight of diamond paste and about 20% by weight of aluminum oxide to form second grinding region 130 having a thickness of about 2 µm to about 3 µm.

The abrasive used to form second grinding region 130 is different from that used to form first grinding region 120, since the thickness of second grinding region 130 is more precisely controlled than the thickness of first grinding region 120. When, in the process of grinding first grinding region 120, orange light is observed in fifth region V of FIG. 11 using a transmission scope, second grinding region 130 has a thickness of about 2 µm to about 3 µm.

The process for forming second grinding region 130 is referred to as a coarse process. The process of forming second grinding region 130 is coarser than the process of forming third grinding region 140, and preliminary specimen 110 is planarized by the coarse process to expand an area to be analyzed by the TEM.

The method of forming the dimple further comprises grinding second grinding region 130 to form third grinding region 140 (413).

Figure 16:
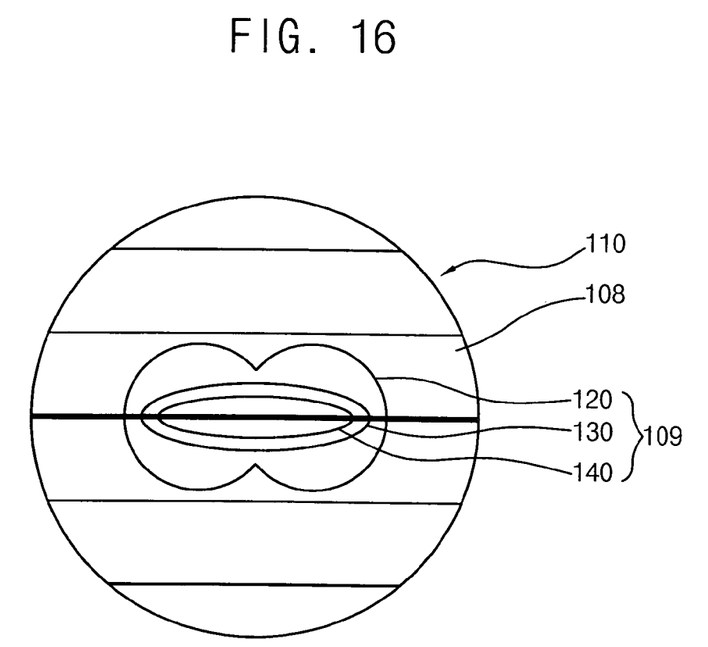

Referring to FIGS. 10 and 16, second grinding region 130 is ground with respect to the analysis point to form third grinding region 140 having an elliptical shape that has the third area smaller than the second area of second grinding region 130. The major axis of third grinding region 140 is substantially along the line of analysis of preliminary specimen 110.

In this exemplary embodiment, second grinding region 130 is ground using an abrasive comprising aluminum oxide to form third grinding region 140 having a thickness of no more than about 1 µm.

The abrasive used to form third grinding region 140 is different from that used to form second grinding region 130, since the thickness of third grinding region 140 is more precisely controlled than the thickness of second grinding region 130. When, in grinding second grinding region 130, yellow light or white light is observed in sixth region VI of FIG. 11 using a transmission scope, third grinding region 140 has a thickness of no more than about 1 µm.

Here, to prepare the TEM specimen for analysis, a coarse surface of second grinding region 130 having fine scratches is minutely polished using aluminum oxide to form third grinding region 140 having the dimple. The major axis of third grinding region 140 has a length of about 50 µm to about 150 µm.

First, second and third grinding regions 120, 130 and 140 together form dimple region 109.

Figure 17:
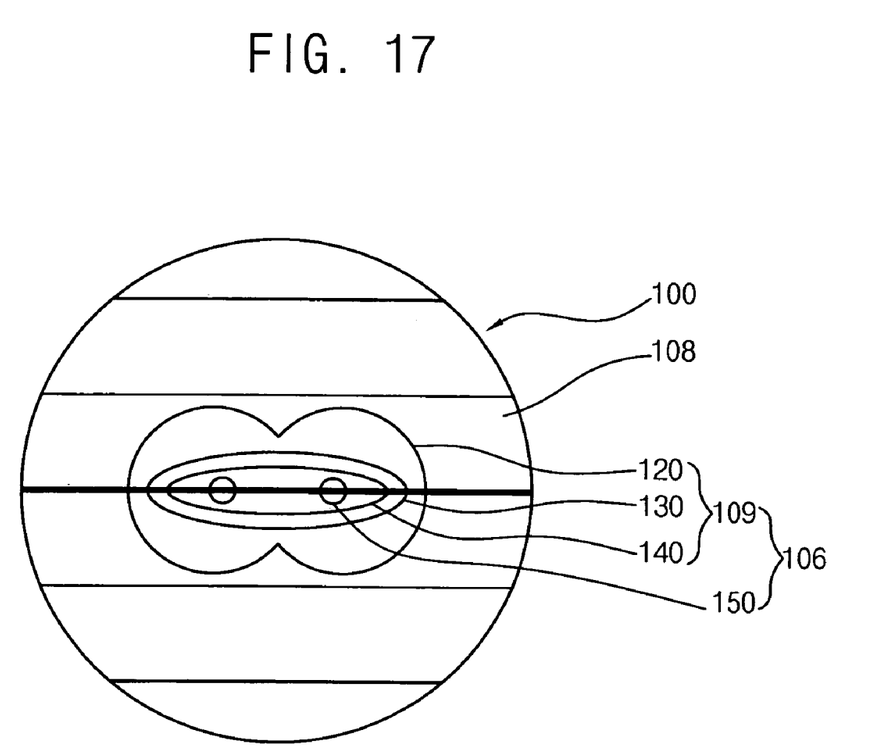

Referring to FIGS. 9 and 17, an ion-milling process is performed on preliminary specimen 110 to complete specimen 100 having ion-milling region 150 (420).

In detail, third grinding region 140 is sputtered using argon ions to form two holes corresponding to ion-milling region 150. The holes are arranged along the line of analysis.

As a result, dimple region 109 including first, second, and third grinding regions 120, 130, and 140 and ion-milling region 150 together form analysis region 106, thereby completing specimen 100.

Specimen 100 is then placed on a table. Electrons are transmitted through the holes of ion milling region 150 to test specimen 100. Third grinding region 140 of specimen 100 is mainly observed. Analysis region 106 of specimen 100, in accordance with an exemplary embodiment, has a width of about 50 µm to about 150 µm, which is generally wider than the width of 30 µm to about 50 µm of the conventional specimen.

A specimen in accordance with exemplary embodiments of the invention has a relatively large analysis region. Thus, even if the dimple region is not aligned with the center point of the specimen, or the holes have very large diameters, the specimen may still be readily analyzed.

Although exemplary embodiments of the invention have been described, it will be apparent to those of ordinary skill in the art that modifications and variations can be made while remaining within the scope of the invention as set forth in the following claims.

What is claimed is:

1. A method of manufacturing a transmission electron microscope (TEM) specimen, comprising:
preparing a preliminary specimen; and,
forming a specimen by forming a dimple region on a surface portion of the preliminary specimen, and ion milling the preliminary specimen having the dimple region to form an ion-milling region within the dimple region,
wherein preparing the preliminary specimen comprises:
cutting a first and a second patterned wafer,
cutting a first, a second, a third, and a fourth dummy wafer;
forming the first face of the first patterned wafer on the first face of the second patterned wafer;
forming the first, second, third, and fourth dummy wafers on second faces opposite the first faces of first and second patterned wafers to form a stacked specimen;
slicing the stacked specimen in a direction substantially perpendicular to the first faces of the first and second patterned wafers to form a sliced specimen;
punching the sliced specimen to form a circular specimen; and
grinding the circular specimen to form the preliminary specimen.

2. The method of claim 1, wherein forming the dimple region comprises:

grinding the preliminary specimen to form a first grinding region having a first area, a first length, and a first width smaller than the first length;

grinding the first grinding region to form a second grinding region having a second area smaller than the first area, a second length, and, a second width smaller than the second length; and, grinding the second grinding region to form a third grinding region having a third area smaller than the second area, a third length, and a third width smaller than the third length, wherein each of the first, second, and third lengths are substantially along a line of analysis, and each of the first, second, and third widths are substantially perpendicular to the line of analysis.

3. The method of claim 2, wherein each of the first, second and third grinding regions has an elliptical shape or an overlapping circular shape.

4. The method of claim 2, wherein the third length of the third grinding region is about 50 µm to about 150 µm.

5. The method of claim 2, wherein the first grinding region has a thickness of about 10 µm to about 20 µm.

6. The method of claim 2, wherein the second grinding region has a thickness of about 2 µm to about 3 µm.

7. The method of claim 2, wherein the third grinding region has a thickness of no more than about 1 µm.

8. The method of claim 1, wherein the ion-milling region comprises two separate holes having an analysis point between them.

9. A method of manufacturing a transmission electron microscope (TEM) specimen, comprising:

preparing a preliminary specimen; and, forming a specimen by forming a dimple region on a surface portion of the preliminary specimen, and ion milling the preliminary specimen having the dimple region to form an ion-milling region within the dimple region, wherein preparing the preliminary specimen comprises:
  cutting a first and a second patterned wafer;
  forming a stacked specimen, wherein forming the stacked specimen comprises forming the first face of the first patterned wafer on the first face of the second patterned wafer;
  slicing the stacked specimen in a direction substantially perpendicular to the first faces of the first and second patterned wafers to form a sliced specimen;
  punching the sliced specimen to form a circular specimen; and,
  grinding the circular specimen to form the preliminary specimen.

10. The method of claim 9, wherein forming the dimple region comprises:
  grinding the preliminary specimen to form a first grinding region having a first area, a first length, and a first width smaller than the first length;
  grinding the first grinding region to form a second grinding region having a second area smaller than the first area, a second length, and a second width smaller than the second length; and,
  grinding the second grinding region to form a third grinding region having a third area smaller than the second area, a third length, and a third width smaller than the third length,
  wherein each of the first, second, and third lengths are substantially along a line of analysis, and each of the first, second, and third widths are substantially perpendicular to the line of analysis.

11. The method of claim 10, wherein each of the first, second and third grinding regions has an elliptical shape or an overlapping circular shape.

12. The method of claim 10, wherein the third length of the third grinding region is about 50 µm to about 150 µm.

13. The method of claim 10, wherein the first grinding region has a thickness of about 10 µm to about 20 µm.

14. The method of claim 10, wherein the second grinding region has a thickness of about 2 µm to about 3 µm.

15. The method of claim 10, wherein the third grinding region has a thickness of no more than about 1 µm.

16. A method of manufacturing a transmission electron microscope (TEM) specimen, comprising:

preparing a preliminary specimen;

wherein preparing the preliminary specimen comprises:
  cutting a first and a second patterned wafer;
  forming a stacked specimen, wherein forming the stacked specimen comprises forming the first face of the first patterned wafer on the first face of the second patterned wafer;
  slicing the stacked specimen in a direction substantially perpendicular to the first faces of the first and second patterned wafers to form a sliced specimen;
  punching the sliced specimen to form a circular specimen; and,
  grinding the circular specimen to form the preliminary specimen; and
  forming a specimen by forming a dimple region on a surface portion of the preliminary specimen, and ion milling the preliminary specimen having the dimple region to form an ion-milling region within the dimple region, wherein:
  forming the dimple region comprises grinding the preliminary specimen to form a first grinding region having a first area, a first length, a first width smaller than the first length, and an overlapping circular shape;
  the first length is substantially along a line of analysis; and,
  the first width is substantially perpendicular to the line of analysis.

17. The method of claim 16, wherein the ion-milling region comprises two separate holes having an analysis point between them.

18. The method of claim 16, wherein forming the dimple region further comprises:
  grinding the first grinding region to form a second grinding region having a second area smaller than the first area, a second length, and a second width smaller than the second length; and,
  grinding the second grinding region to form a third grinding region having a third area smaller than the second area, a third length, and a third width smaller than the third length,
  wherein each of the second and third lengths are substantially along the line of analysis, and each of the second and third widths are substantially perpendicular to the line of analysis.

19. The method of claim 16, wherein each of the second and third grinding regions has an elliptical shape or an overlapping circular shape.

* * * * *